US006268167B1

(12) United States Patent
Wild et al.

(10) Patent No.: US 6,268,167 B1
(45) Date of Patent: *Jul. 31, 2001

(54) METHODS FOR DETERMINING AN ANALYTE IN A PLASMA OR SERUM SAMPLE WHICH MAY BE CONTAMINATED WITH INTERFERING SUBSTANCES RESULTING FROM HEMOLYSIS

(75) Inventors: Thomas Wild, Weilheim; Friederike Weber; Christoph Berding, both of München; Wilhelm Kleider, Murnau, all of (DE)

(73) Assignee: Roche Diagnostics GmbH, Mannheim (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/963,563

(22) Filed: Nov. 3, 1997

Related U.S. Application Data

(63) Continuation of application No. 08/510,363, filed on Aug. 2, 1995, now abandoned.

(30) Foreign Application Priority Data

Aug. 3, 1994 (DE) ................................................ 44 274 92

(51) Int. Cl.[7] ....................................................... C12Q 1/32
(52) U.S. Cl. .............................. 435/26; 356/320; 436/175
(58) Field of Search ................................ 435/26; 356/39, 356/40, 320, 409; 364/498; 436/66, 175

(56) References Cited

U.S. PATENT DOCUMENTS

| 4,263,512 | * | 4/1981 | Sagusa et al. ........................ 250/373 |
| 4,728,604 | | 3/1988 | Moller ..................................... 435/16 |
| 5,416,026 | * | 5/1995 | Davis ..................................... 436/66 |
| 5,420,042 | * | 5/1995 | Schafer et al. ........................ 436/517 |
| 5,590,052 | * | 12/1996 | Kopf-Sill et al. ..................... 364/498 |

FOREIGN PATENT DOCUMENTS

| 2847176 | | 6/1979 | (DE) . |
| 0139985 | | 5/1985 | (EP) . |
| 0268025 | | 5/1988 | (EP) . |
| 0 268 025 | * | 5/1988 | (EP) . |
| 2026692 | | 2/1980 | (GB) . |

OTHER PUBLICATIONS

Davy C., The Effect of Haemolysis on Some Clinical Chemistry Parameters in the Marmoset, Laboratory Animals 18:161–168, 1984.*
Sagusa, Toshiyuki, "Automatic Analyzer" (Abstract), *Patent Abstracts of Japan 12: 368*, p. 766 (Apr. 10, 1988).

* cited by examiner

*Primary Examiner*—Ralph Gitomer
(74) *Attorney, Agent, or Firm*—Fulbright & Jaworski, LLP

(57) ABSTRACT

In order to analyze a medical sample while avoiding error contributions due to hemolysis, prior to the main reaction for a component present in the sample, a pre-reaction is produced and measured by which the degree of hemolysis in the sample is determined and the result of the sample to be determined that is subsequently obtained is corrected by this error contribution using the relationship (correlation) that has been found between the degree of hemolysis and the error contribution.

10 Claims, 7 Drawing Sheets

SPIKING EXPERIMENTS WITH A HAEMOLYSATE USING 20 SERA, WITHOUT REDUCTION

| SEREN | SERUM(UI) | WDF % | +50 * | +100 * | +150 * | +200 * | +250 * | +300 * | +400 * | +500 * |
|---|---|---|---|---|---|---|---|---|---|---|
| 1 | 24.15 | 100.0% | 101.6% | 107.7% | 108.9% | 116.3% | 124.5% | 130.3% | 141.7% | 152.5% |
| 2 | 20.37 | 100.0% | 105.2% | 109.8% | 114.1% | 122.6% | 126.7% | 136.0% | 150.3% | 166.0% |
| 3 | 16.08 | 100.0% | 130.7% | 110.9% | 117.4% | 122.6% | 133.5% | 141.4% | 165.3% | 177.9% |
| 4 | 16.96 | 100.0% | 104.6% | 112.6% | 119.2% | 128.9% | 133.8% | 143.0% | 169.3% | 182.0% |
| 5 | 21.66 | 100.0% | 102.7% | 110.6% | 112.0% | 118.8% | 125.2% | 130.4% | 148.6% | 157.7% |
| 6 | 17.18 | 100.0% | 102.0% | 110.9% | 118.1% | 128.5% | 132.0% | 146.6% | 160.0% | 174.4% |
| 7 | 21.21 | 100.0% | 103.7% | 107.4% | 113.5% | 117.9% | 125.5% | 130.6% | 145.0% | 158.6% |
| 8 | 33.15 | 100.0% | 106.7% | 101.9% | 110.3% | 112.5% | 115.4% | 120.9% | 132.5% | 139.2% |
| 9 | 48.05 | 100.0% | 103.0% | 104.6% | 107.6% | 109.9% | 113.1% | 115.3% | 123.0% | 127.2% |
| 10 | 24.16 | 100.0% | 104.2% | 107.2% | 115.6% | 119.1% | 127.2% | 130.1% | 143.8% | 154.0% |
| 11 | 34.48 | 100.0% | 104.4% | 106.0% | 108.9% | 111.5% | 117.0% | 119.6% | 131.8% | 134.4% |
| 12 | 33.75 | 100.0% | 106.0% | 106.0% | 110.5% | 114.0% | 117.5% | 121.7% | 134.4% | 140.4% |
| 13 | 43.17 | 100.0% | 102.1% | 105.5% | 109.2% | 109.9% | 113.2% | 115.5% | 122.5% | 125.9% |
| 14 | 85.86 | 100.0% | 103.7% | 104.7% | 106.5% | 106.9% | 110.3% | 111.8% | 115.2% | 118.3% |
| 15 | 221.20 | 100.0% | 99.9% | 100.8% | 102.6% | 102.1% | 103.6% | 105.1% | 102.4% | 105.2% |
| 16 | 59.00 | 100.0% | 105.3% | 103.7% | 105.7% | 107.5% | 109.3% | 112.2% | 117.3% | 122.3% |
| 17 | 57.42 | 100.0% | 101.4% | 106.5% | 105.6% | 106.7% | 110.2% | 111.3% | 117.7% | 122.5% |
| 18 | 20.32 | 100.0% | 106.6% | 110.9% | 117.2% | 123.3% | 130.3% | 139.9% | 155.5% | 170.5% |
| 19 | 14.54 | 100.0% | 105.9% | 112.8% | 121.0% | 129.3% | 144.1% | 147.3% | - | - |
| 20 | 13.72 | 100.0% | 108.1% | 113.6% | 124.1% | 131.9% | 144.8% | - | - | - |

\* mg / dl HAEMOGLOBIN

FIG. 3

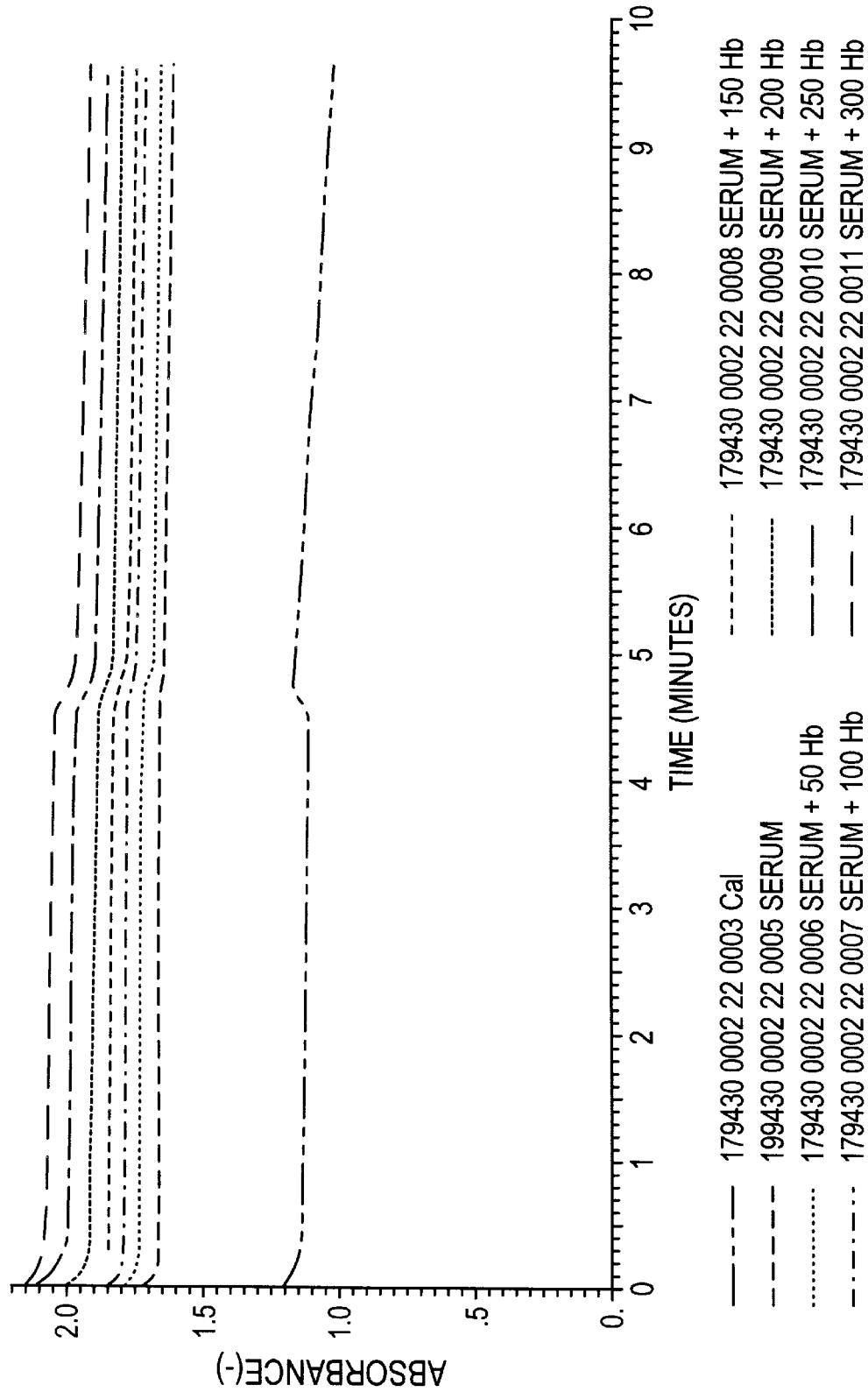

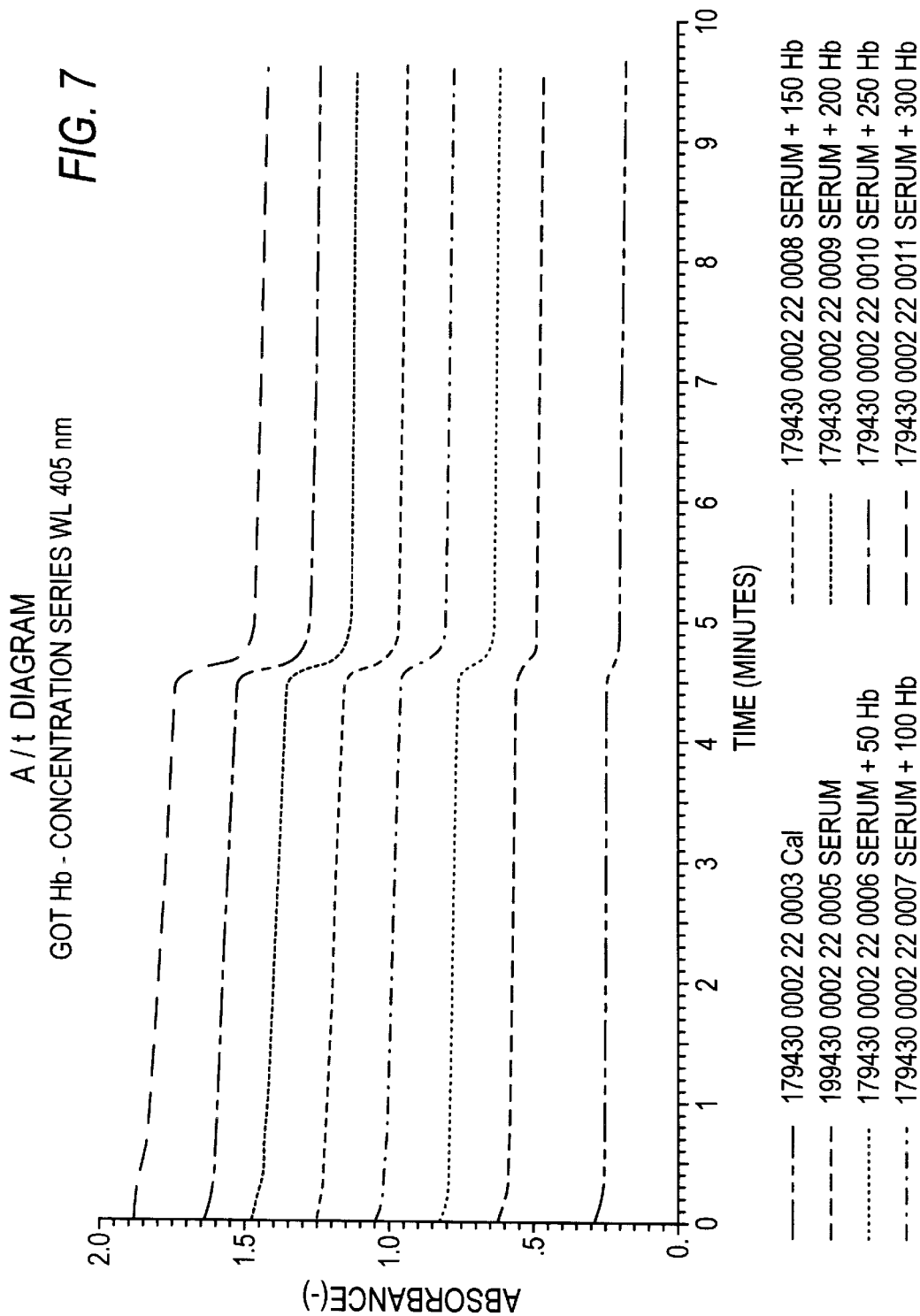

METHODS FOR DETERMINING AN ANALYTE IN A PLASMA OR SERUM SAMPLE WHICH MAY BE CONTAMINATED WITH INTERFERING SUBSTANCES RESULTING FROM HEMOLYSIS

This application is a continuation of application Ser. No. 08/510,363, filed Aug. 2, 1995, abandoned.

The present invention concerns a method for the analysis of a medical sample while avoiding measurement errors due to haemolysis.

The most common test material for biochemical analyses is blood serum or plasma. It is known that errors can occur in the determination of various analytes from blood serum or blood plasma which influence the result of the measurement and which are caused by the properties of the sample. Measurement errors in this sense are caused in particular by hemolytic sample material. Hemolysis in blood samples can substantially falsify the analytical measurement results.

If hemolysis occurs in a blood sample then some of the red blood corpuscles have been destroyed and the constituents released in this process contaminate the sample material. As a consequence of this the analytical serum or plasma values are rendered inaccurate by the constituents of the blood corpuscles such as e.g. haemoglobin.

In order to eliminate this disadvantage U.S. Pat. No. 4,263,512 proposes the determination of the interfering chromogen in a blood sample together with the analyte and recommends correction of the measurement error according to the extent of haemolysis (correlates with the chromogen concentration). However, this conventional correction method only takes into account the red blood pigment released by the erythrocytes in order to determine the measurement error in haemolytic sample material. EP-0 268 025 B1 points out that there is a quantitative relationship between the extent of interference by haemolysis, the analyte concentration and the measurement error caused by the interference. This relationship can be expressed with the aid of multiple regression. The correction factors derived from this fit then enable the analytical result to be corrected on the basis of a hemolysis interference determined independently e.g. by measurement of the Hb value (while ignoring other possible dependencies on analyte concentration).

The clinical chemical analyzer "Synchron CX 5" from the Beckman Company utilizes a set of 2 to 5 wavelengths to measure reaction time courses and to compensate for interfering background. Suitable selection of additional, non-reaction-relevant wavelengths enables an automatic correction for endogeneous spectral interferences. At 16 second intervals an eight flash photometric measurement is carried out, i.e. in the case of a maximum of 5 wavelengths 8×5=40 mesurement data are generated. The following polychromatic equation is then used for the signal correction:

$$\text{Absorbance difference} = \text{difference}(A-B-C-D-E+k)$$

in which

A=change in the absorbance of the bichromatically measured analyte reaction

B–E=weighted bichromatic correction wavelengths and k=constant which enables the spectral influence of sera in the absence of lipemia, haemolysis or icterus to be taken into account.

Depending on the automated analyzer, the polychromatic correction can either be carried out categorically (Beckman analyzer) when it is part of a test application or only when a test-specific limit has been exceeded above which the interference error has a marked influence on sample recovery.

However, the object of the present invention is to provide an analytical method which enables measurement errors caused by contaminating components in a blood serum sample or in a blood plasma sample of haemolytic blood to be determined with improved accuracy and considerably less laboriously than conventional correction methods.

This object is achieved by a method for analysing a medical sample while avoiding measurement errors due to hemolysis in which, before the actual photometric determination of a component present in the sample, the sample is subjected to a pre-reaction in which the extent of hemolysis in the sample is determined and the measured value of the component to be determined obtained subsequently is corrected by a value which has been determined by correlating the extent of hemolysis with the measurement error contribution of interfering components.

A distinguishing feature of the method according to the invention compared to the state of the art is the advantage that an independent determination of the degree of hemolysis, e.g. by determining the haemoglobin value in a sample, is not necessary for the correction of the measured value of a haemolytic sample. Moreover a relationship was found between the degree of hemolysis of a sample and the pre-reaction determined in hemolytic sera or plasma. In this case the pre-reaction occurs in the presence of sample and a reagent but before adding the start reagent of the actual measurement determination.

It is possible with the aid of the biometric model described in the present invention to directly estimate the degree of hemolysis of a sample from the pre-reaction which it causes and to carry out a corresponding correction of the analytical result. A further contribution to the error which must be taken into consideration for the analysis is the fact that an incorrect result for hemolytic samples can also be obtained when determining particular substances when this substance is also present in red blood corpuscles and as a result is also additionally present in the sample to be analysed after hemolysis. This contribution to the measurement error is also taken into account by the method according to the invention since, in addition to the degree of hemolysis, the content of analyte in the sample also enters into the pre-reaction.

The method according to the invention enables correction of measurement errors due to hemolysis and is particularly efficient at correcting in the reference range (31 U/l in women, 37 U/l in men) (<10% increase in recovery (see FIG. 1)).

In addition, beyond the reference range, interferences of up to an order of magnitude of 80% obtained with methods according to the state of the art could be reduced to less than 30% using the appropriate correction.

In the method according to the invention the pre-reaction alone takes into account the individual properties of the sample so that, on the basis of the previous experimental data, it is unnecessary to carry out further specific correction processes for the sample material. In particular additional measurements are not required. This is an important advantage compared to the previously described correction methods for hemolytic sera or plasmas.

In a preferred embodiment of the invention the pre-reaction is also determined photometrically. In this case it is particularly preferred that the photometric determination is carried out bichromatically and in particular at $340/405$ nm and that the actual measured value is derived from the difference between the results of the two wavelengths.

The pre-reaction is preferably started by addition of a reagent which contains NADH and LDH (lactate dehydrogenase). In a particularly preferred embodiment the reagent additionally contains MDH (malate dehydrogenase).

In a further preferred embodiment of the present invention the reliability of the relationship between the degree of hemolysis determined by the pre-reaction and the contribution to the measurement error caused by the interfering components such as hemoglobin in particular or by the component to be determined which is, however, present in the sample as a result of haemolysis is ensured on a broad basis for a large group of test persons with a heterogeneous state of health, age and sex.

In a particularly preferred method the relationship between the pre-reaction and the main reaction with regard to the component to be determined is defined with the aid of the formula $$rate_{substance/sample} = rate_{total} - rate_{pre-reaction} - rate_{substance/erythrocytes}$$

in which substance denotes the component to be determined in the sample.

One possibility for eliminating interference can be ascertained with the aid of a mathematical relationship between the pre-reaction and the main reaction. A schematic reaction time course is shown in FIG. 2 and the mathematical relationship for the total reaction is $$rate_{total} = rate_{substance/sample} + rate_{substance/erythrocytes} + rate_{pre-reaction}$$

in which substance refers to the component to be determined which is either present in the serum or in erythrocytes. This means that the change in the measured value per unit of time (total kinetics) is composed of the signal of the hemolysis-free serum as well as that of the erythrocytes and the pre-reaction which continues after addition of the actual determination reagent. In order to calculate the interference-free serum value from this, the formula must be solved as follows:

$$rate_{substance/sample} = rate_{total} - rate_{substance/erythrocytes} - rate_{pre-reaction}$$

and leads to the aforementioned formula for determining $rate_{substance/sample}$.

The created data set can be used in the following model for calculating the $rate_{substance/erythrocytes}$ based on a multiple linear regression:

$$rate_{substance/erythrocytes} = \alpha \times rate_{pre-reaction} + \beta \times (rate_{pre-reacton})^2$$

(see FIG. 4)

Within the scope of the present invention it is particularly preferred that the formula necessary for calculating the corrected value is stored on a data carrier and that this is used to automatically correct the analytical results with the aid of electronic data processing.

It is particularly preferable when the value of the measurement error can already be calculated from the information stored on the data carrier. For this purpose the data which have been determined on a large group of test persons for the relationship between the degree of haemolysis determined by the pre-reaction and the measurement error contribution are stored on the data carrier.

It is especially preferred to use the method in such a way that the corrected value for the component that is subject to interference is displayed on the print-out and/or on the display of the electronic data processing that is used for the measurement. In this case it is in turn preferable to state the corrected value together with a tolerance range. However, it may be expedient to only allow the measured value to be automatically corrected within particular tolerance limits and to carry out corrections outside these tolerance limits manually after appropriate consideration of the circumstances.

The method according to the invention is especially preferred used for components to be determined which are selected from (a) the group of analytes which can be detected in a manner corresponding to that of the GOT/GPT biochemical reaction type and/or (b) which belong to a group of analytes comprising total protein, albumin, LDH, potassium, total cholesterol, free cholesterol, uric acid, triglycerides, sodium, chloride, β-lipoproteins, thymol turbidity tests, zinc sulphate turbidity tests, phospholipids and free fatty acids. In this case it is also possible, and this is a preferred embodiment of the invention, to determine a component whose concentration in red blood cells is higher than in blood serum or in blood plasma.

The method according to the invention is thus an easily automated and rapid procedure for determining components present in blood, blood serum or plasma samples and thereby avoid measurement errors due to haemolysis wherein only a pre-reaction is carried out in addition to the actual determination reaction which enables the determination of the degree of haemolysis.

The present invention is elucidated further by the attached figures and examples.

BRIEF DESCRIPTION OF THE FIGURES

FIG. 3 summarizes results from a spiking experiment, where hemolyzed serum samples were spiked with enzyme GOT, and then assayed, without correction.

FIG. 6 shows measurements in accordance with the invention, at 340 nm.

FIG. 7 shows measurements, in accordance with the invention, at 405 nm.

DETAILED DESCRIPTION OF PREFERRED EMBODIMENTS

EXAMPLE 1

Experiments for the determination of glutamate-oxaloacetate transaminase (GOT)

There is a strong interference of GOT activity by hemolytic sample material and this leads to false positive results. There is a clear dependency between the degree of hemolysis and increase in GOT activity. At serum values of ca. 20 U/l and at a Hb value of 500 mg/dl, GOT is measured 80% too high by methods according to the state of the art. This interference is mainly due to the fact that GOT is present in erythrocytes and thus there is a direct relationship between the degree of hemolysis and increase in activity.

Principle of the GOT test:

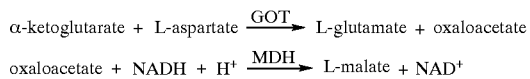

The measurement is carried out at 340 nm (main wavelength) and 405 nm (secondary wavelength). The NADH degradation is detected.

Hemolysate Preparation 1:

Collect blood (heparinized plasma)/centrifuge/discard supernatant/wash blood cake three times with 0.9% NaCl and rupture erythrocytes with water and filter over glass wool/determine Hb content.

This was used to spike serum of the same donor.

Hemolysate Preparation 2:

Collect blood (serum)/centrifuge/store serum/add glass beads to the blood cake and stir vigorously for 2–3 hours/ centrifuge (the glass beads serve as a separation layer between cell residues and hemolysate)/remove supernatant by pipette and determine Hb content.

The following results were obtained using the hemolysate preparation 2 with 20 different sera in different concentration ranges.

The above-mentioned sera were spiked in 8 steps: 50, 100, 150, 200, 250, 300, 400, 500 mg/dl Hb (FIG. 3).

The measurements were carried out on the Hitachi 717 clinical chemical analyzer using measurement points 10–20 (pre-reaction) and 30–50 (main reaction).

In order to validate the correction procedure described above, first a panel of non-hemolytic human sera were measured on the Hitachi 717 analyzer and the determined GOT activities were defined as BM target values.

Subsequently 25 sera from this panel with up to 8 different additions of hemolysate (a total of 217 samples) were measured.

Figure 1:
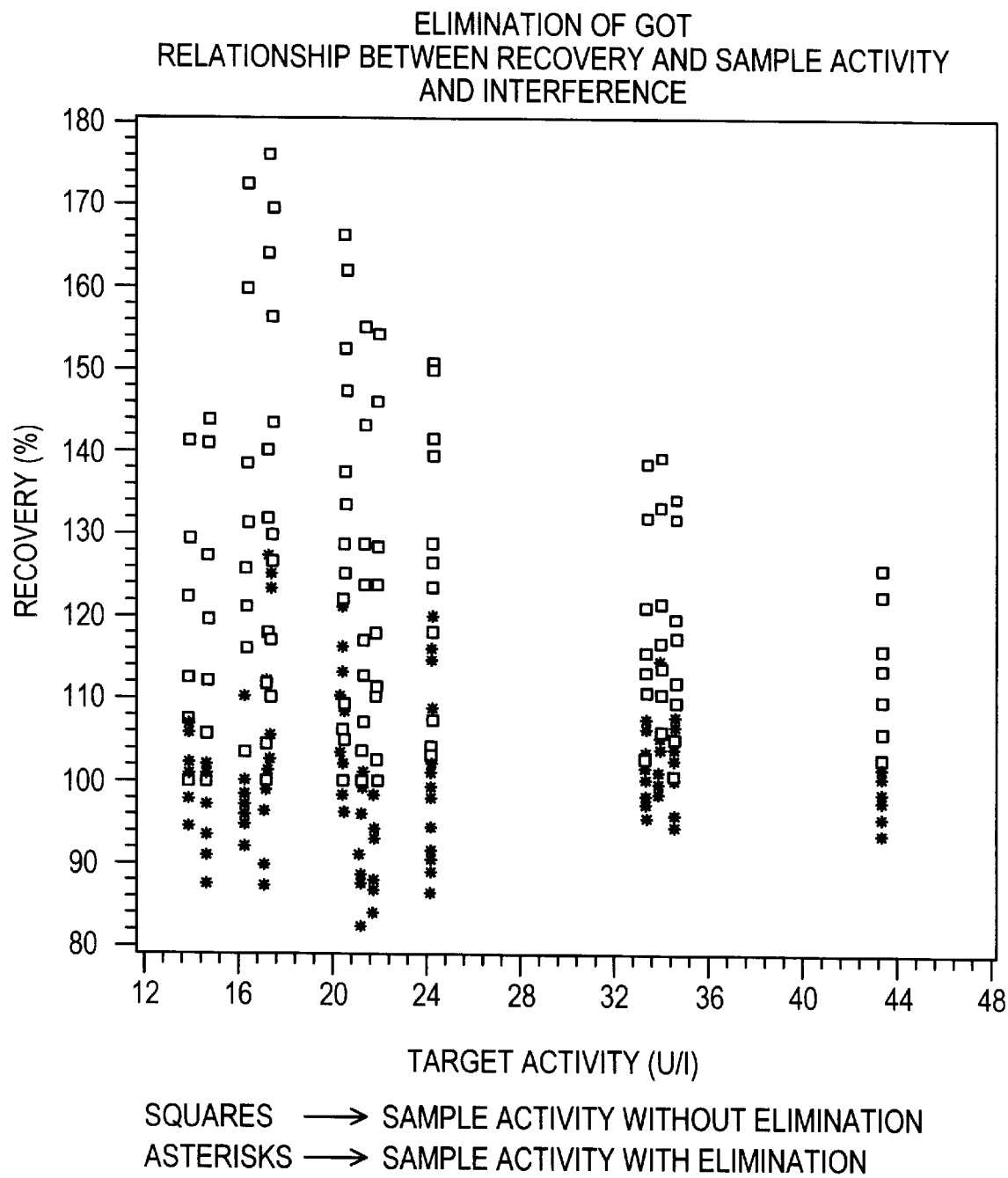
FIG. 1 presents data wherein individual measured values for a target analyte in blood samples are determined. Small squares are values where interference is not eliminated, and asterisks are representative of values where it is eliminated.
Figure 2:
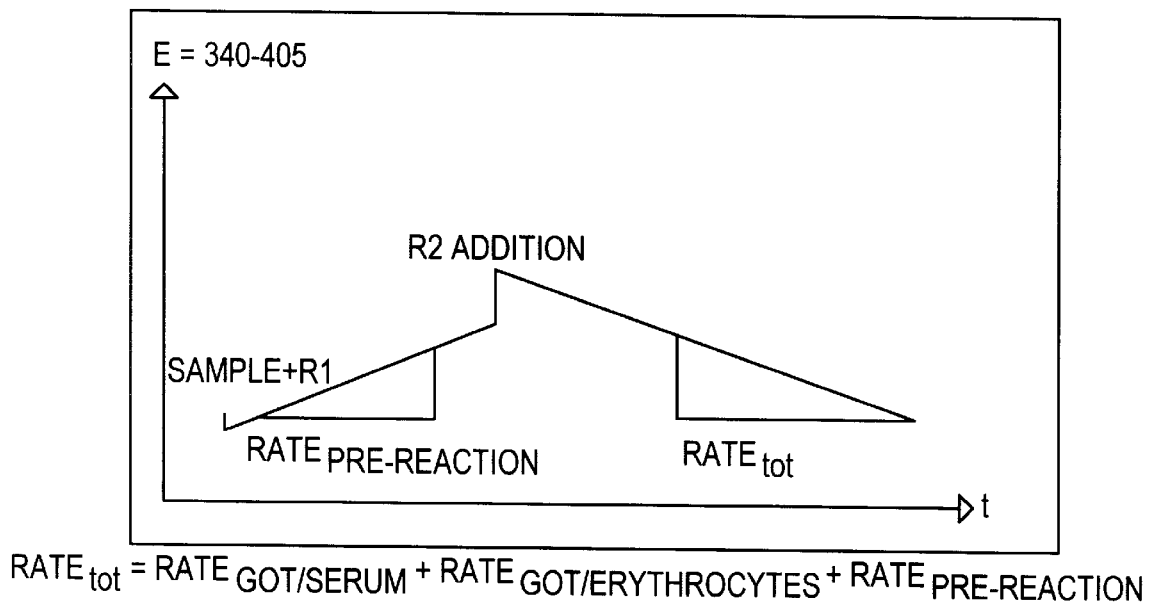
FIG. 2 shows a schematic, reaction time course for the method of the invention.
Figure 4:
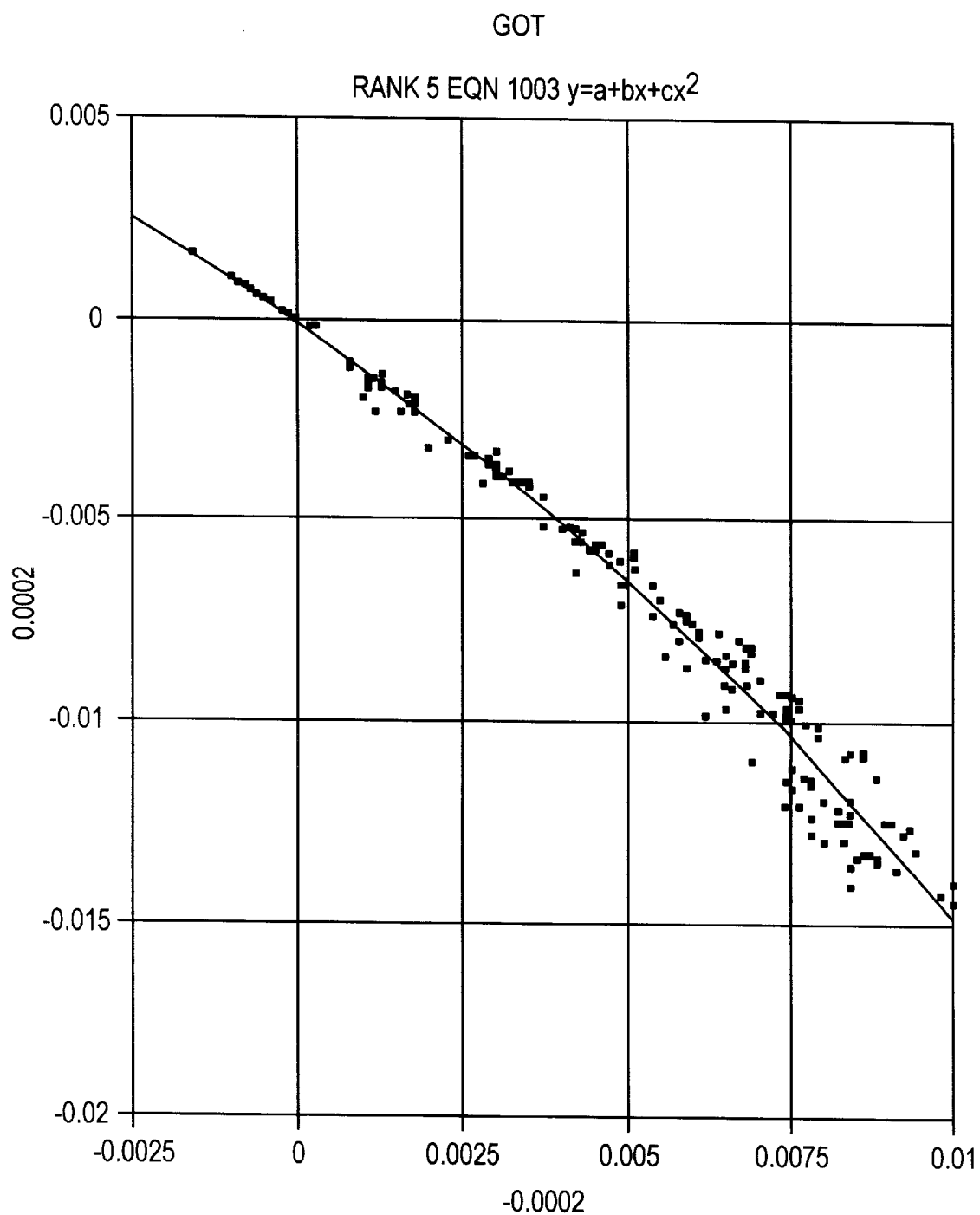
FIG. 4 shows the results obtained when the correction procedure of the example was used in the samples of FIG. 3. The graph compares target value and actual value, with and without the procedure.
Figure 5:
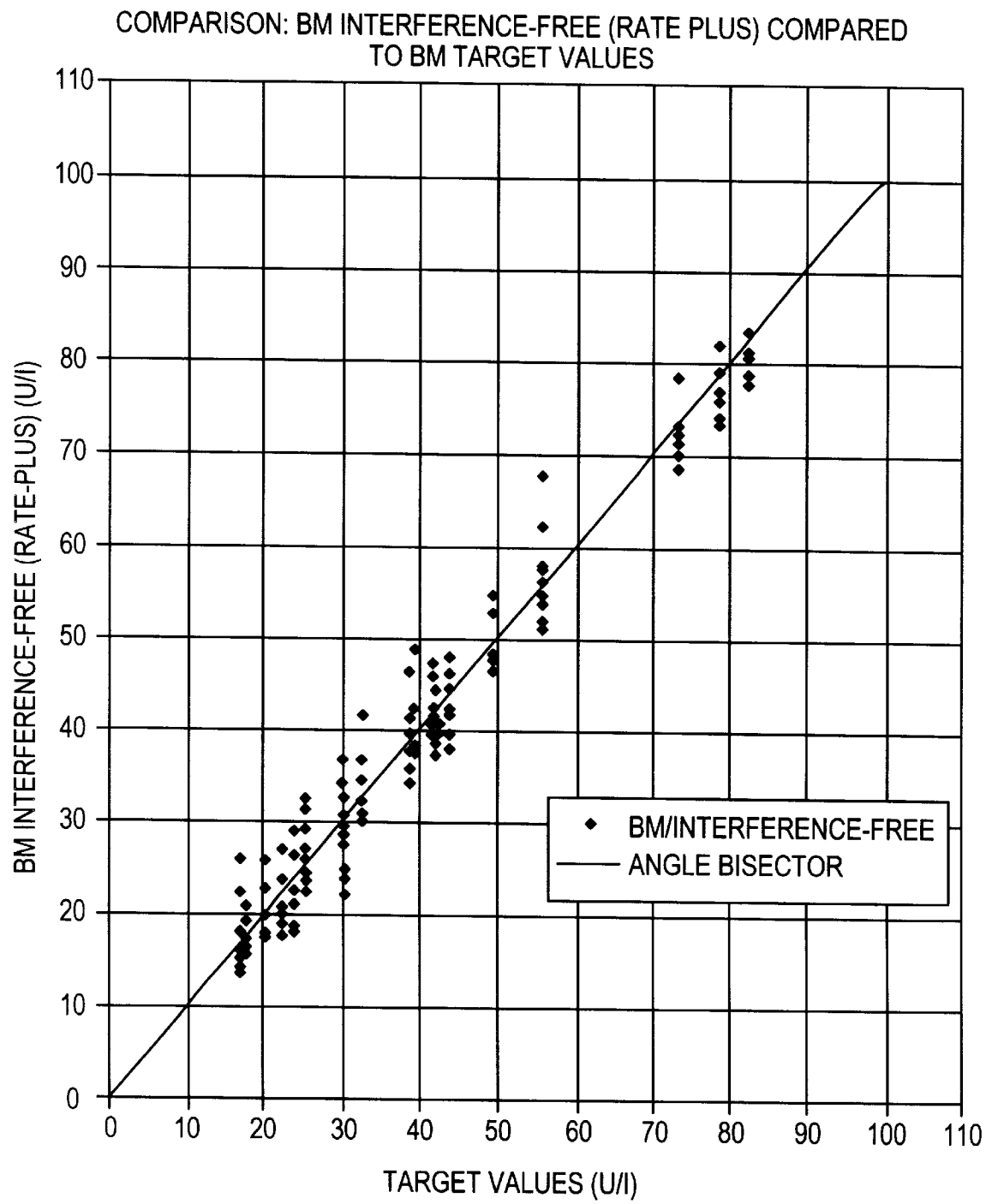
FIG. 5 shows correlation between target and actual value.

The method comparisons between the corresponding measured values for non-hemolytic ("target value") and haemolytic sample material ("actual value") with and without the correction procedure are shown in FIG. 4 (correlation between target and actual values=0.923) and FIG. 5 (correlation between target and actual values=0.981). This result, which was reproduced several times, clearly shows that hemolytic interference can be efficiently corrected by means of the method stated here.

| Explanation of the pre-reaction: | |
|---|---|
| 1. Influence of the reagent | |
| Composition of reagent 1: | |
| 1. Sodium monohyrdogen phosphate | |
| 2. Sodium dihydrogen phosphate | buffer A |
| 3. L(+)-monosodium aspartate | |
| 4. LDH | |
| 5. NADH | enzyme tablets + fillers |
| 6. MDH | |
| Preservative: Na azide | |

In substitution experiments it was possible to explain the cause of the increase in the pre-reaction at $^{340}/_{405}$ and how the main reaction behaves in this case:

| Buffer + haemolytic sample | Pre-reaction | Main reaction |
|---|---|---|
| Original | ⇈ | ⇊ |
| Buffer A | — | — |
| Buffer A + LDH | — | — |
| Buffer A + MDH | — | — |
| Buffer A + NADH | ⇊ | ⇊ |
| Buffer A + LDH + MDH + NADH | ⇈ | ⇊ |
| Buffer A + MDH + LDH | — | — |
| Buffer A + MDH + NADH | ⇊ | ⇊ |
| Buffer A + LDH + NADH | ⇈ | ⇊ |

Two up arrows indicate a massive increase, and one up arrow means an increase. Similarly, two down arrows indicate a massive decrease and one down arrow, a decrease.

When reagent R1 is added to a hemolytic sample a pre-reaction with a signal increase occurs as the degree of hemolysis increases. The measurement is carried out bichromatically at $^{340}/_{405}$ nm.

If the same measurement is carried out at 340 nm then no pre-reaction is found. In contrast, a reaction with a decreasing signal occurs at 405 nm (FIGS. 6 and 7). Thus the increasing pre-reaction results by forming the difference between the two wavelengths.

What is claimed is:

1. A method for determining an analyte in a sample of patient's plasma or serum, which sample can be contaminated by hemolysis products from the hemolysis of red blood cells, the method sequentially comprising:

(i) adding NADH and LDH to the sample to induce a pre-reaction which converts NADH to $NAD^+$;

(ii) photometrically measuring the sample at 340 nm and 405 nm to photometrically determine the conversion of NADH to $NAD^+$ and thereby the degree of hemolysis in the sample;

(iii) inducing a main reaction in the sample by adding a determination reagent that determines the analyte in the sample and photometrically measuring the rate of said main reaction at 340 nm and 405 nm;

(iv) correcting the rate of the main reaction with a correction factor indicative of the degree of hemolysis in the sample as determined in step (ii) to obtain a corrected value, wherein said corrected value is indicative of the amount of said analyte in said sample.

2. The method of claim 1, wherein said correction factor is:

$$\text{rate}_{analyte\ in\ said\ sample} = \text{rate}_{total} - \text{rate}_{pre-reaction} - \text{rate}_{analyte/erythrocytes},$$

wherein $\text{rate}_{total}$ is the total rate after steps (i) to (iii).

3. The method of claim 1, in which the correlation between the degree of hemolysis as determined by said prereaction and the contribution of said hemolysis to the measurement error have been determined.

4. The method of claim 1, further comprising adding malate dehydrogenate in step (i).

5. The method of claim 1, comprising calculating the corrected analyte value by electronic data processing.

6. The method of claim 1, wherein said analyte comprises an analyte which is determined according to the GOT/GPT biochemical reaction principle.

7. The method of claim 1, wherein said analyte is selected from the group consisting of total protein, albumin, lactate dehydrogenate, potassium, total cholesterol, free cholesterol, uric acid, triglyceride, sodium, chloride, β-lipoprotein, phospholipids, and free fatty acids.

8. The method of claim 1, wherein said analyte is an analyte determinable in a thymol turbidity test, or a zinc sulphate turbidity test.

9. The method of claim 1, wherein said analyte is an analyte which occurs in red blood cells at a concentration higher than said analyte occurs in serum or plasma.

10. The method of claim 1, wherein the correction factor for the pre-reaction is derived from data obtained from a large group of test persons.

* * * * *